(12) United States Patent
Kim et al.

(10) Patent No.: US 11,761,894 B2
(45) Date of Patent: Sep. 19, 2023

(54) SILICON-RHODAMINE FLUORESCENT PROBE CONTAINING HYDROPHOBIC GROUP AND USE THEREOF

(71) Applicant: AJOU UNIVERSITY INDUSTRY—ACADEMIC COOPERATION FOUNDATION, Suwon-si (KR)

(72) Inventors: Eunha Kim, Seoul (KR); Wook Kim, Suwon-si (KR); Jong Hyun Kim, Suwon-si (KR); June Sung, Siheung-si (KR); Jun Gi Rho, Ansan-si (KR)

(73) Assignee: AJOU UNIVERSITY INDUSTRY—ACADEMIC CORPORATION FOUNDATION, Suwon-si (KR)

( * ) Notice: Subject to any disclaimer, the term of this patent is extended or adjusted under 35 U.S.C. 154(b) by 601 days.

(21) Appl. No.: 16/860,540

(22) Filed: Apr. 28, 2020

(65) Prior Publication Data
US 2020/0340920 A1    Oct. 29, 2020

(30) Foreign Application Priority Data
Apr. 29, 2019    (KR) .................. 10-2019-0049788

(51) Int. Cl.
| | |
|---|---|
| *C07F 7/08* | (2006.01) |
| *G01N 21/64* | (2006.01) |
| *G01N 33/50* | (2006.01) |
| *C09K 11/06* | (2006.01) |

(52) U.S. Cl.
CPC ....... *G01N 21/6428* (2013.01); *C07F 7/0816* (2013.01); *C09K 11/06* (2013.01); *G01N 21/6458* (2013.01); *G01N 33/5014* (2013.01); *C09K 2211/1007* (2013.01); *C09K 2211/1018* (2013.01); *G01N 2021/6439* (2013.01)

(58) Field of Classification Search
CPC .................................................. C07F 7/0816
See application file for complete search history.

(56) References Cited

FOREIGN PATENT DOCUMENTS

| | | |
|---|---|---|
| WO | 2018/101473 A1 | 6/2018 |
| WO | 2018/135598 A1 | 7/2018 |

OTHER PUBLICATIONS

Sung, et al. Bioconjugate Chem. 2019, 30, 210-217.*
Eunha Kim et al., Red Si-rhodamine drug conjugates enable imaging in GFP ells, Chem. Commun., Mar. 13, 2014, vol. 50, pp. 4504-4507 (4 pages total).
Jacek Zielonka et al., "Mitochondria-Targeted Triphenylphosphonium-Based Compounds: Syntheses, Mechanisms of Action, and Therapeutic and Diagnostic Applications", Chemical Reviews, Jun. 27, 2017, vol. 117, pp. 10043-10120 (78 pages total).
Grazvydas Lukinavicius et al., "A near-infrared fluorophore for live-cell super-resolution microscopy of cellular proteins", Nature Chemistry, Feb. 2013, vol. 5, pp. 132-139 (9 pages total).
Michael P. Murphy, "Targeting lipophilic cations to mitochondria", Biochimica et Biophysica Acta 1777, Apr. 8, 2008, pp. 1028-1031 (4 pages total).

* cited by examiner

*Primary Examiner* — Shawquia Jackson
(74) *Attorney, Agent, or Firm* — Sughrue Mion, PLLC (57) ABSTRACT

The present invention relates to a novel near-infrared fluorescent probe having specificity for mitochondria due to a hydrophobic group attached to a silicon-rhodamine core, and the use thereof for mitochondrial detection and cancer diagnosis. The fluorescent probe of the present invention has improved mitochondrial targeting efficiency compared to conventional probes due to a hydrophobic group attached to a silicon-rhodamine core, can detect mitochondria in living tissue with high sensitivity and specificity in a near-infrared (NIR) region (700 to 1,700 nm), and can acquire three-dimensional high-resolution biological images without harming the human body. Due to these advantages, the fluorescent probe can be used not only for mitochondrial detection in cells in the laboratory, but also as a contrast agent or a drug delivery carrier in cancer diagnosis and surgery.

9 Claims, 7 Drawing Sheets
(5 of 7 Drawing Sheet(s) Filed in Color)

SILICON-RHODAMINE FLUORESCENT PROBE CONTAINING HYDROPHOBIC GROUP AND USE THEREOF

CROSS REFERENCE TO RELATED APPLICATIONS

This application claims the benefit of the priority based on Korean Patent Application No. 10-2019-0049788 filed Apr. 29, 2019, of which the content is incorporated herein by reference.

BACKGROUND OF THE INVENTION

Field of the Invention

The present invention relates to a silicon-rhodamine fluorescent probe containing a hydrophobic group and the use thereof, and more particularly, to a novel near-infrared fluorescent probe having specificity for mitochondria due to a hydrophobic group attached to a silicon-rhodamine core, and the use thereof for mitochondrial detection and cancer diagnosis.

Description of the Related Art

Mitochondria provide cellular energy by generating adenosine triphosphate (ATP) via oxidative phosphorylation. In addition, they play important roles in cell signaling including modulation of ROS production, regulation of apoptotic cell death, and maintenance of redox homeostasis, innate immunity and autophagy. Consequently, mitochondrial dysfunction results in a number of human conditions ranging from neurodegenerative diseases to atherosclerosis, and diabetes.

Mitochondria are surrounded by a double-membrane, comprising an inner and an outer membrane, and mitochondrial morphology varies considerably between different cell types. In live cells, mitochondrial morphology is continuously modified by the combined action of fission and fusion events, crucial to maintain mitochondrial function under cellular stress. Therefore, the morphology of mitochondria is dependent on the cell function and disease states. Recent studies indicated that mitochondrial morphology can be utilized as a biological marker for the diagnosis of cancer phenotypes and to monitor drug response. Consequently, there is a high demand for fluorescent mitochondrial bioprobes allowing for the investigation of cell signaling and serving as molecular diagnostic tools.

The large difference in membrane potential (positive in the mitochondrial intermembrane space and negative in the mitochondrial matrix) across the mitochondrial inner membrane can be efficiently exploited for targeting the compounds to mitochondria. Therefore, most fluorescent bioprobes for mitochondria are based on compound conjugation with lipophilic cations (typically triphenyl phosphonium ion) (Zielonka, J. et al., (2017) Mitochondria-Targeted Triphenylphosphonium-Based Compounds: Syntheses, Mechanisms of Action, and Therapeutic and Diagnostic Applications. *Chemical Reviews* 117, 10043-10120), allowing for the efficient transfer of molecules through lipid bilayers and their accumulation in the mitochondrial matrix (Murphy, M. P. (2008) Targeting lipophilic cations to mitochondria. *Biochimica et Biophysica Acta (BBA)—Bioenergetics* 1777, 1028-1031). However, systematic studies addressing the effect of hydrophobicity on the efficiency of mitochondrial targeting by specific fluorophores are rarely reported. Therefore, developing fluorescent probes to monitor mitochondrial function can be a difficult task, as it must be preceded by proper optimization. In this context, the present inventors reasoned that systematic modification of fluorophore hydrophobicity could provide an excellent guide for future development of efficient and versatile mitochondrial fluorescent probes. In addition, considering the growing interest in mitochondria specific drug delivery, this strategy would help developing theragnostic chemical tools, especially for diseases involving mitochondria.

Under this technical background, the present inventors have made extensive efforts to develop a near-infrared fluorescent probe for mitochondrial staining, and as a result, have found that various fluorescent probes, which display similar photophysical properties but have different hydrophobicities, could be synthesized by adding 10 different commercial amines to a silicon-rhodamine core, and the novel fluorescent probes thus synthesized can exhibit excellent effects on mitochondrial staining and distinguish a cancer cell line from a normal cell line, thereby completing the present invention.

PRIOR ART DOCUMENTS

Non-Patent Documents (Non-Patent Document 1) Zielonka, J. et al., (2017) Mitochondria-Targeted Triphenylphosphonium-Based Compounds: Syntheses, Mechanisms of Action, and Therapeutic and Diagnostic Applications. Chemical Reviews 117, 10043-10120.

(Non-Patent Document 2) Murphy, M. P. (2008) Targeting lipophilic cations to mitochondria. Biochimica et Biophysica Acta (BBA)—Bioenergetics 1777, 1028-1031.

SUMMARY OF THE INVENTION

It is an object of the present invention to provide a novel compound in which a hydrophobic group is attached to a silicon-rhodamine core, and the use thereof for mitochondria targeting.

To achieve the above object, the present invention provides a compound represented by the following Formula 1:

[Formula 1]

wherein R represents a hydrophobic group.

The present invention also provides a probe for mitochondrial targeting represented by the following Formula 1:

[Formula 1]

wherein R represents a hydrophobic group.

The present invention also provides a composition for mitochondrial detection comprising the probe.

The present invention also provides a contrast agent comprising the probe.

The present invention also provides a composition for cancer diagnosis comprising the probe.

The present invention also provides a drug delivery carrier comprising the probe.

The present invention also provides a method for visualizing mitochondria in cells in vitro, the method comprising steps of:

injecting the probe into cells in vitro; and measuring a detectable fluorescent signal generated in the cells.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Unless otherwise defined, all the technical and scientific terms used in the present specification have the same meanings as commonly understood by those skilled in the art to which the present disclosure pertains. In general, the nomenclature used in the present specification is well known and commonly used in the art.

Mitochondria provide cellular energy by utilizing the proton electrochemical gradient potential generated by the respiratory electron transport chain (ETC) across the mitochondrial membrane. Electron transport, occurring at the inner mitochondrial membrane, provides the energy required by pumps to translocate proton ions from the mitochondrial matrix to the intermembrane space (complexes I, III, and IV) Therefore, the most straightforward approach for targeting mitochondria is the generation of lipophilic cations allowing for probe accumulation inside the mitochondrial matrix by the electrochemical gradient.

To develop a new near-IR mitochondria targeting bioprobe, the present inventors selected SiR-Me as the lipophilic cationic fluorochrome. Since silicon substitution of the oxygen atom in the rhodamine fluorochrome shifts the emission wavelength of SiR to the NIR range (>680 nm) preserving the small size of the molecule (MW≈470), the present inventors reasoned that SiR-Me would be a suitable fluorochrome for a systematic evaluation of the effect of probe hydrophobicity on the efficiency of mitochondria targeting.

Starting with 3-bromoaniline, compound 2 was synthesized by a facile one-pot synthesis process, including lithiation, silylanization and oxidation of compound 1. The reaction between compound 2 and lithiated compound 3, followed by acidic deprotection, resulted in the desired SiR-Me compound (compound 4). Afterward, the present inventor conjugated SiR-Me with 10 different commercial amines to generate a library of SiR-Me analogs (SiR-Mito) with various cLogP values, reflecting different hydrophobicity (Table 1).

TABLE 1

Photophysical properties, cLogP value, and correlation coefficient for the colocalization of SiR-Mito probes with MitoTracker green.

| cpd. | R | M.W. | Ex/Em (nm) | Φ | clogP | Mitochondria Targeting[a] |
|---|---|---|---|---|---|---|
| SiR-Mito 1 | 2-Hydroxy ethyl | 486.3 | 661/668 | 0.32 | 2.29 | N.D. |
| SiR-Mito 2 | Ethyl | 470.3 | 662/668 | 0.40 | 3.38 | * |
| SiR-Mito 3 | n-Butyl | 498.3 | 652/665 | 0.29 | 4.44 | — |
| SiR-Mito 4 | Benzyl | 532.3 | 651/666 | 0.30 | 4.82 | * |
| SiR-Mito 5 | Phenylethyl | 546.3 | 651/669 | 0.29 | 4.95 | * |
| SiR-Mito 6 | Cyclohexylmethyl | 538.3 | 651/668 | 0.30 | 5.50 | *** |
| SiR-Mito 7 | tert-Octyl | 554.4 | 650/667 | 0.29 | 5.94 | *** |
| SiR-Mito 8 | Cyclooctyl | 552.3 | 651/668 | 0.33 | 6.00 | *** |
| SiR-Mito 9 | Cyclohexylethyl | 552.3 | 652/666 | 0.26 | 6.03 | *** |
| SiR-Mito 10 | 2-Methylheptyl | 554.4 | 654/667 | 0.27 | 6.33 | *** |

[a]N.D.: not determined.
*//* indicate the Pearson coefficient values for colocalization test between the probes and MitoTracker green.
* $0.7 \leq R < 0.8$;
** $0.8 \leq R < 0.9$;
*** $0.9 \leq R$ The resulting library exhibited a molecular weight range from 470.3 to 554.4 dalton and a cLogP value range from 2.29 to 6.55. The present inventors confirmed that conjugation of the different amines by an amide linkage resulted in probes with different hydrophobicity but similar photophysical properties such as excitation (654±4 nm) wavelength, emission (667±1 nm) wavelength and quantum yield (0.31±0.05).

Therefore, in one aspect, the present invention is directed to a compound represented by the following Formula 1:

[Formula 1]

wherein R represents a hydrophobic group.

In the present invention, R may be selected from the group consisting of 2-hydroxyl ethyl, ethyl, n-butyl, benzyl, phenylethyl, cyclohexylmethyl, tert-octyl, cyclooctyl, cyclohexylethyl, and 2-methylheptyl, but is not limited thereto.

Meanwhile, co-staining with each compound synthesized according to the present invention and a commercial green fluorescent mitochondrial probe was performed, and as a result, it was confirmed that the compounds of the present invention could specifically stain mitochondria, like the green fluorescent mitochondrial probe. It was observed that this mitochondria-specific targeting was somewhat different depending on the hydrophobicity of the probes and that the silicon-rhodamine fluorescent probe having a cyclooctyl group attached thereto particularly exhibited the highest mitochondrial targeting efficiency.

Therefore, in another aspect, the present invention is directed to a probe for mitochondrial targeting represented by the following Formula 1:

[Formula 1]

wherein R represents a hydrophobic group.

In the present invention, R may be selected from the group consisting of 2-hydroxyl ethyl, ethyl, n-butyl, benzyl, phenylethyl, cyclohexylmethyl, tert-octyl, cyclooctyl, cyclohexylethyl, and 2-methylheptyl, but is not limited thereto.

In the present invention, the probe may be a near-infrared fluorescent probe. The use of fluorescent probes has an advantage over other medical imaging technologies in that it can acquire three-dimensional high-resolution biological images without harming the human body. Also, fluorescence imaging in the near-infrared (NIR) region (700-1700 nm) has increased the penetration depth of biological tissues through various technological advances. In addition, the probe according to the present invention has a relatively small molecular weight of 486 to 554 Daltons, which is relatively smaller in size than a conventional mitochondrial probe having a near-infrared emission wavelength, and thus the physical properties required for medical imaging technology are improved. Thus, the probe according to the present invention may be used as a solid cancer marker suitable for fluorescent molecular tomography.

In the present invention, it has been confirmed that the hydrophobicity of the probe has a significant effect on the efficiency of mitochondrial targeting. Thus, the probe may have a c log P value of 2.29 to 6.33, preferably 5.50 to 6.33, but is not limited thereto.

In still another aspect, the probe for mitochondrial targeting according to the present invention provides a composition for mitochondrial detection comprising the probe.

In yet another aspect, the probe for mitochondrial targeting according to the present invention provides a method for visualizing mitochondria in cells in vitro, the method comprising steps of:

injecting the probe into cells in vitro; and measuring a detectable fluorescent signal generated in the cells.

In an embodiment according to the present invention, the detectable fluorescent signal is a near-infrared signal.

In addition, it was confirmed that the probe of the present invention was capable of distinct mitochondria-specific staining even in living HeLa and Hep3B cells, and could successfully distinguish the hepatocellular carcinoma cell line Hep3B, from the normal cell line L02.

Therefore, in yet another aspect, the present invention is directed to a contrast agent comprising the probe.

The probe of the present invention is useful for contrast imaging in a condition such as a tumor (or cancer), and is particularly useful for diagnosis of various solid tumors (breast cancer, liver cancer, uterine cancer, etc.) and in image-guided surgery. In addition, the probe of the present invention can be usefully used to deliver a mitochondria-targeting drug suitable for the relevant condition and to monitor the effect of the drug delivered by various other methods on the condition.

Therefore, in still another aspect in addition to the contrast agent, the present invention provides a composition for cancer diagnosis.

In the present invention, the composition for cancer diagnosis can diagnose cancer by distinguishing cancer cells from normal cells by using the difference in fluorescence intensity generated by binding of the probe to the normal cells and the cancer cells. In an Example of the present invention, it was shown that the difference in fluorescence intensity between liver cancer Hep3B cells and normal liver cells (L02 or Chang cells) was about 5.9-fold, but the difference in fluorescence intensity between normal cells was not significant because the p value in t-test was high.

Therefore, in the present invention, the composition for cancer diagnosis may be characterized in that it diagnoses cancer if the fluorescence intensity of cells to be tested increases by 1.5 times or more compared to that of normal cells, and preferably if the fluorescence intensity of cells to be tested increase by 2 times or more.

In yet another aspect, the present invention provides a drug delivery carrier comprising the probe.

In another aspect, the present invention provides a method for visualizing a tumor in an animal, the method comprising steps of: administering to the animal the composition comprising the probe; and measuring a detectable signal generated in the animal, wherein the detectable signal is associated with specific labeling of the tumor by mitochondrial targeting.

In one embodiment of the present disclosure, the detectable signal is a fluorescent signal, preferably a near-infrared fluorescent signal.

In one embodiment of the present disclosure, the animal may be mammals including humans.

Methods of administering the contrast agent or composition to animals are well known to those skilled in the art. In a preferred embodiment, the formulation may be administered by injection, although any other suitable means of administration is contemplated within the scope of the present invention.

In some embodiments, the method of the present invention comprises the step of measuring the detectable signal generated in the animal. Methods of measuring the detectable signal include, without limitation, imaging methods, for example, fluorescence imaging methods. In some embodiments, the fluorescence imaging system is, for example, a Xenogen IVIS 100 system, an IVIS spectral system (PerkinElmer, Waltham, Mass.), or any other suitable noninvasive, in vivo fluorescent imaging system. In some embodiments, the detectable fluorescence signal is measured using a da Vinci surgical system (Intuitive Surgical, Inc., Sunnyvale, Calif.). As described in more detail below, such a system can be used to implement the present labeling and visualization methods in combination with an intraoperative fluorescence induced surgical technique in patient tissue treated with the imaging agent.

In yet another aspect, the present invention provides a compound for use in labeling tissue in an animal. The compound is described in detail above. The compound in combination with a pharmaceutically acceptable carrier is administered to an animal to label tissue. The compound is also provided to visualize a tumor in an animal. As described above, the compound in combination with a pharmaceutically acceptable carrier is administered to an animal, and a detectable signal generated in the animal by mitochondrial targeting of the compound is measured to visualize a tumor.

As used herein, the term "targeting" means that the probe of the present invention specifically interacts with an object to be detected and distinguishes the object from other objects. In a preferred embodiment of the present invention, the probe is positioned or distributed specifically in mitochondria in a cell or tissue sample in vivo or in vitro and distinguishes the mitochondria from other objects in the cell or tissue sample by staining the mitochondria. For example, the probe of the present invention targets mitochondria, is positioned or distributed specifically in the mitochondria, and stains the mitochondria, and thus a drug may be connected directly or indirectly to the probe, so that the probe may be used to deliver the drug into cells. In addition, the probe may be used to monitor drug reactions by detecting the change in morphology or number of intracellular mitochondria caused by the response of cells or tissues in the course of treatment after administration of drugs.

As used herein, the term "detection" refers to identifying the presence or absence of an object with which the probe of the present invention specifically interacts. More specifically, the term "detection" refers to identifying the presence or absence of mitochondria. Based on the fact that the probe of the present invention can specifically detect mitochondria, the present invention can exhibit a positive correlation between the amount of mitochondria present in a sample and the fluorescence intensity generated by the probe. As an example, since the fluorescence intensity is stronger in cancer (tumor) cells (or tissues) in which the amount of mitochondria is greater than in normal cells (or tissues), the probe of the present invention can be used as a composition for cancer diagnosis.

Hereinafter, the present invention will be described in more detail with reference to examples. It will be obvious to those skilled in the art that these examples are merely to illustrate the present invention, and the scope of the present invention is not limited by these examples.

Example 1. Compound Synthesis

All reactions were carried out under an atmosphere of nitrogen or argon in air-dried glassware with magnetic stirring. Air- and/or moisture-sensitive liquids were transferred with syringe. Organic solutions were concentrated by rotary evaporation at 25-60° C. at 15-30 torr. All solvents and common materials were purchased from suppliers and used without further purification. Column chromatography was carried out as "Flash Chromatography" using Biotage MPLC machine. $^1$H NMR and $^{13}$C NMR data were recorded on an JEOL ECZ-600R Magnetic Resonance System (600 MHz) in Ajou University. Recorded shifts are reported in parts per million (δ): Chemical shift, multiplicity (s=singlet, d=doublet, t=triplet, q=quartet, m=multiplet, br=broad), coupling constant (J, Hz) and integration. Low resolution mass spectrometry (LRMS) was obtained by LC/MS system, Finnigan MSQplus Surveyer (Thermo Scientific) or 6120 Quadrupole LC/MS (Agilent Technologies). The progress of reaction was monitored using thin layer chromatography (TLC) (silica gel 60, F254 0.25 mm), and components were visualized by observation under UV light (254 and 365 nm) or by treating the TLC plates with Phosphonolybdic acid (PMA), KMnO$_4$, or ninhydrin followed by heating. Cell culture reagents including fatal bovine serum, culture media, and antibiotic-antimycotic solution were purchased from GIBCO. MitoTracker Green, and Hoechst were purchased from Invitrogen. The culture dish and glassbottom dish were purchased from CORNING, and SPL. All spectra experiments were performed in a 1×1 cm quartz cuvette. Fluorescence emission spectra were recorded on JASCO FP-8200 spectrofluorometer, and UV absorption spectra were recorded on JASCO V-670 spectrophotometer. Absolute quantum yield was measured by QE-2000 (Otsuka Electronics).

1-1. Chemical Synthesis of SiR-Mito Probes

Synthesis of silicon rhodamine core (compound 4 in FIG. 1) was carried out as described in previous study (Kim, E., Yang, K. S., Giedt, R. J., and Weissleder, R. (2014) Red Si-rhodamine drug conjugates enable imaging in GFP cells. *Chem Commun (Camb)* 50, 4504-7).

1-2. General Synthetic Procedure

A solution of compound 4 (1.0 eq), PyBOP (1.3 eq), and DIPEA (3.0 eq) in DMF was stirred for 10 min at room temperature under argon atmosphere. After 10 min, amine analog (2.0 eq) was added to reaction mixture and stirred at room temperature for overnight. The amine derivatives used in the present invention are as follows: 2-hydroxyl ethylamine, ethylamine, n-Butylamine, Benzylamine, Phenylethylamine, cyclohexylmethylamine, tert-octylamine, cyclooctyl amine, cyclohexylethyl amine, 2-methylheptyl amine. Reaction mixture was directly purified with 18C reverse column chromatography with Biotage MPLC. Purification yielded the following compounds:

N-(7-(dimethylamino)-10-(5-((2-hydroxyethyl)carbamoyl)-2-methylphenyl)-5,5-dimethyldibenzo[b,e]silin-3(5H)-ylidene)-N-methylmethanaminium (SiR-Mito 1)

$^1$H NMR (600 MHz, Methanol-d$_4$) δ 7.97 (dd, J=7.2 Hz, 8.4 Hz, 1H), 7.64 (d, J=3.0 Hz, 1H), 7.54 (d, J=7.8 Hz, 1H), 7.38 (d, J=3.0 Hz, 2H), 7.01 (d, J=9.6 Hz, 2H), 6.79 (dd, J=9.0 Hz, 2H), 3.69 (t, J=5.4 Hz, 2H), 3.50 (t, J=5.4 Hz, 2H), 3.35 (s, 12H), 2.10 (s, 3H), 0.62, 0.61 (s, 6H); $^{13}$C NMR (150 MHz, Methanol-d$_4$) δ155.8, 149.5, 142.1, 141.1, 140.4, 133.2, 131.6, 129.0, 128.8, 128.4, 122.3, 115.4, 61.5, 43.6, 40.9, 19.4, -1.2, -1.3.

N-(7-(dimethylamino)-10-(5-(ethylcarbamoyl)-2-methylphenyl)-5,5-dimethyldibenzo[b,e]silin-3(5H)-ylidene)-N-methylmethanaminium (SiR-Mito 2)

$^1$H NMR (600 MHz, Methanol-d$_4$) δ7.95 (dd, J=7.8 Hz, 1H), 7.61 (d, J=1.8 Hz, 1H), 7.53 (d, J=7.8 Hz, 1H), 7.38 (d, J=3 Hz, 2H), 7.06 (d, J=9.6 Hz, 2H), 6.79 (dd, J=9.6 Hz, 2H), 3.41 (t, J=7.2 Hz, 2H), 3.35 (s, 12H), 2.10 (s, 3H), 1.21 (t, J=6.6 Hz, 3H); $^{13}$C NMR (150 MHz, Methanol-d$_4$) δ169.3, 169.0, 155.8, 149.5, 142.1, 141.0, 140.4, 133.3, 131.6, 129.0, 128.7, 128.4, 122.3, 115.4, 40.9, 35.9, 19.4, 14.9, -1.2, -1.3.

N-(10-(5-(butylcarbamoyl)-2-methylphenyl)-7-(dimethylamino)-5,5-dimethyldibenzo[b,e]silin-3(5H)-ylidene)-N-methylmethanaminium (SiR-Mito 3)

$^1$H NMR (600 MHz, Methanol-d$_4$) δ7.95 (dd, J=7.2 Hz, 1H), 7.61 (d, J=2.4 Hz, 1H), 7.53 (d, J=8.4 Hz, 1H), 7.39 (d, J=2.4 Hz, 2H), 7.06 (d, J=9.6 Hz, 2H), 6.79 (dd, J=9.6 Hz, 2H), 3.37 (t, J=7.2 Hz, 2H), 3.35 (s, 12H), 2.10 (s, 3H), 1.59 (t, J=7.2 Hz, 2H), 1.40 (q, J=7.8 Hz, 2H), 0.96 (t, J=7.8 Hz, 3H), 0.62 (s, 6H); $^{13}$C NMR (150 MHz, Methanol-d$_4$) δ167.9, 167.6, 154.5, 148.2, 140.8, 139.6, 139.1, 132.0, 130.3, 127.6, 127.4, 127.0, 121.0, 114.0, 39.6, 39.5, 31.3, 19.9, 18.1, 12.8, -2.5, -2.6.

N-(10-(5-(benzylcarbamoyl)-2-methylphenyl)-7-(dimethylamino)-5,5-dimethyldibenzo[b,e]silin-3(5H)-ylidene)-N-methylmethanaminium (SiR-Mito 4)

$^1$H NMR (600 MHz, Methanol-d$_4$) δ7.96 (dd, J=8.4 Hz, 1H), 7.62 (d, J=2.4 Hz, 1H), 7.51 (d, J=8.4 Hz, 1H), 7.35 (d, J=3.0 Hz, 2H), 7.29 (m, 5H), 7.03 (d, J=3.6 Hz, 2H), 6.76 (dd, J=9.6 Hz, 2H), 4.53 (s, 2H), 3.32 (s, 12H), 2.07 (s, 3H), 0.58 (s, 6H); $^{13}$C NMR (150 MHz, Methanol-d$_4$) δ169.2, 168.9, 155.8, 149.5, 142.1, 141.2, 140.5, 140.1, 133.1, 131.8, 129.5, 129.1, 128.8, 128.6, 128.4, 128.2, 122.3, 115.4, 44.6, 40.9, 19.5, -1.2.

N-(10-(5-((cyclohexylmethyl) carbamoyl)-2-methylphenyl)-7 (dimethylamino)-5,5-dimethyldibenzo[b,e]silin-3(5H)-ylidene)-N-methylmethanaminium (SiR-Mito 5)

$^1$H NMR (600 MHz, Methanol-d$_4$) δ7.95 (dd, J=7.8 Hz, 1H), 7.61 (d, J=2.4 Hz, 1H), 7.53 (d, J=8.4 Hz, 1H), 7.38 (d, J=2.4 Hz, 2H), 7.06 (d, J=10.2 Hz, 2H), 6.79 (dd, J=9.6 Hz, 2H), 3.34 (s, 12H), 3.21 (d, J=6.6 Hz, 2H), 2.10 (s, 3H), 1.76 (m, 6H), 1.28 (m, 3H), 0.99 (m, 2H), 0.62 (s, 6H); $^{13}$C NMR (150 MHz, Methanol-d$_4$) δ169.3, 169.1, 155.8, 149.5, 142.1, 141.0, 140.4, 133.4, 131.6, 129.0, 128.7, 128.4, 122.3, 115.4, 47.4, 40.9, 39.3, 32.1, 27.6, 27.0, 19.5, -1.2.

N-(7-(dimethylamino)-5,5-dimethyl-10-(2-methyl-5-(phenethylcabamoyl)phenyl)dibenzo[b,e]silin-3(5H)-ylidene)-N-methylmethanaminium (SiR-Mito 6)

$^1$H NMR (600 MHz, Methanol-d$_4$) δ7.90 (dd, J=10.2 Hz, 1H), 7.55 (d, J=2.4 Hz, 1H), 7.52 (d, J=1.8 Hz, 1H), 7.38 (d, J=2.4 Hz, 2H), 7.24 (m, 5H), 7.04 (d, J=9.6 Hz, 2H), 6.79 (d, J=9.6 Hz, 2H), 3.58 (t, J=7.8 Hz, 2H), 3.35 (s, 12H), 2.90 (t, J=7.8 Hz, 2H), 2.09 (s, 3H), 0.62 (s, 6H); $^{13}$C NMR (150 MHz, Methanol-d$_4$) δ167.9, 167.7, 154.5, 148.2, 140.8, 139.7, 139.2, 139.0, 132.0, 130.3, 128.5, 128.1, 127.7, 127.3, 127.0, 126.0, 121.0, 114.0, 41.3, 39.6, 35.2, 18.1, -2.5, -2.6.

N-(7-(dimethylamino)-5,5-dimethyl-10-(2-methyl-5-((2,4,4-trimethylpentan-2-yl)carbamoyl)phenyl)dibenzo[b,e]silin-3(5H)-ylidene)-N-methylmethanaminium (SiR-Mito 7)

$^1$H NMR (600 MHz, Methanol-d$_4$) δ 7.86 (dd, J=8.4 or 7.2 Hz, 1H), 7.53 (d, J=1.2 Hz, 1H), 7.50 (s, 1H), 7.38 (d, J=2.4 Hz, 2H), 7.05 (d, J=10.2 Hz, 2H), 6.78 (dd, J=10.2 Hz, 2H), 3.35 (s, 12H), 3.16 (m, 6H), 2.91 (s, 1H), 2.08 (s, 3H), 1.94 (s, 2H), 1.85 (m, 6H), 1.48 (s, 6H), 1.01 (s, 9H), 0.61, 0.60 (6H); $^{13}C$ NMR (150 MHz, Methanol-$d_4$) δ169.5, 168.9, 155.8, 149.6, 142.2, 140.5, 140.2, 134.9, 131.4, 129.0, 128.7, 128.4, 122.3, 115.3, 56.8, 51.2, 47.4, 47.4, 43.8, 40.9, 32.6, 31.9, 30.0, 27.4, 27.3, 19.4, −1.2.

N-(10-(5-((cyclooctylmethyl) carbamoyl)-2-methylphenyl)-7-(dimethylamino)-5,5-dimethyldibenzo[b,e]silin-3(5H)-ylidene)-N-methylmethanaminium (SiR-Mito 8)

$^1H$ NMR (600 MHz, Methanol-$d_4$) δ7.95 (dd, J=8.4 Hz, 1H), 7.60 (d, J=1.8 Hz, 1H), 7.52 (d, J=3.0 Hz, 1H), 7.38 (d, J=3.0 Hz, 2H), 7.06 (d, J=3.0 Hz, 2H), 6.79 (dd, J=9.6 Hz, 2H), 4.15 (m, 1H), 3.34 (s, 12H), 2.09 (s, 3H), 1.65 (m, 13H), 0.62, 0.61 (6H); $^{13}C$ NMR (150 MHz, Methanol-$d_4$) δ169.4, 167.8, 155.8, 149.3, 142.2, 140.8, 140.3, 133.60, 131.5, 129.0, 128.9, 128.4, 122.3, 115.4, 51.6, 40.9, 33.4, 28.1, 26.8, 25.2, 19.4, −1.2.

N-(10-(5-((2-cyclohexylethyl) carbamoyl)-2-methylphenyl)-7-(dimethylamino)-5,5-dimethyldibenzo[b,e]silin-3(5H)-ylidene)-N-methylmethanaminium (SiR-Mito 9)

$^1H$ NMR (600 MHz, Methanol-$d_4$) δ7.94 (dd, J=7.2 Hz, 1H), 7.60 (d, J=1.8 Hz, 1H), 7.53 (d, J=7.2 Hz, 1H), 7.38 (d, 3.0 Hz, 2H), 7.06 (d, J=9.6 Hz, 2H), 6.79 (dd, J=9.6 Hz, 2H), 3.40 (t, J=6.6 or 7.8 Hz, 2H), 3.34 (s, 12H), 2.10 (s, 3H), 1.70 (m, 7H), 1.50 (d, J=8.4 Hz, 2H), 1.29 (m, 3H), 0.97 (m, 2H), 0.62, 0.59 (6H); $^{13}C$ NMR (150 MHz, Methanol-$d_4$) δ168.9, 168.5, 155.4, 149.1, 141.8, 140.6, 140.0, 133.0, 131.2, 128.6, 128.3, 128.0, 121.9, 115.0, 40.5, 38.5, 37.6, 36.4, 34.0, 27.3, 27.0, 19.1, −1.6.

N-(7-(dimethylamino)-5,5-dimethyl-10-(2-methyl-5-(octan-2-ylcarbamoyl)phenyl)dibenzo[b,e]silin-3(5H)-ylidene)-N-methylmethanaminium (SiR-Mito 10)

$^1H$ NMR (600 MHz, Methanol-$d_4$) δ8.30 (d, J=8.4 Hz, 1H), 7.95 (dd, J=8.4 Hz, 1H), 7.61 (d, J=2.4 Hz, 1H), 7.53 (d, J=2.4 Hz, 1H), 7.39 (d, J=2.4 Hz, 2H), 7.07 (d, 9.6 Hz, 2H), 6.80 (dd, J=9.6 Hz, 2H), 4.15 (m, 1H), 3.34 (s, 12H), 2.10 (s, 3H), 1.30 (m, 10H), 1.21 (d, J=6.0 Hz, 3H), 0.87 (m, 3H), 0.62, 0.61 (6H); $^{13}C$ NMR (150 MHz, Methanol-$d_4$) δ169.3, 168.5, 155.9, 149.6, 142.2, 142.2, 140.9, 140.3, 133.6, 131.6, 129.0, 128.8, 128.4, 122.3, 155.4, 47.3, 40.9, 17.5, 32.9, 30.2, 27.5, 23.6, 21.0, 19.4, 14.4, −1.2, −1.3.

Example 2. Cell Culture and Fluorescence Microscope Imaging

HeLa human cervical cancer cells were cultured in Dulbecco's modified eagle media (DMEM, GIBCO) containing 10% fetal bovine serum (FBS, GIBCO) and 1% penicillin (GIBCO) at 37° C. in a humidified incubator with 5% $CO_2$. For the fluorescence microscope imaging, cells were harvested using TrypLE™ Express (GIBCO) and resuspended in fresh culture medium. Harvested cells with a density of $4.0×10^3$ cells/well were seeded on a HeLa 96 black well plate (CORNING) and incubated for 24 h. Cells were incubated with SiR-Mito probes (1 μM) and MitoTracker Green (0.5 μM) for 60 min. After the incubation, cells were washed with 1×PBS for three times and observed with inverted fluorescence microscope (DMi8, LEICA). Each experiment was observed using a 325-375 nm exciter, 435-485 nm emitter for DAPI channel, 460-500 nm exciter, 512-542 nm emitter for FITC channel, 541-551 nm exciter, 565-605 nm emitter for Rhodamine channel, and 663-738 nm exciter, 545-625 nm emitter for Cy5 channel.

Example 3. Mitochondria-Targeting Efficiency of Silicon-Rhodamine Probes

Figure 1:
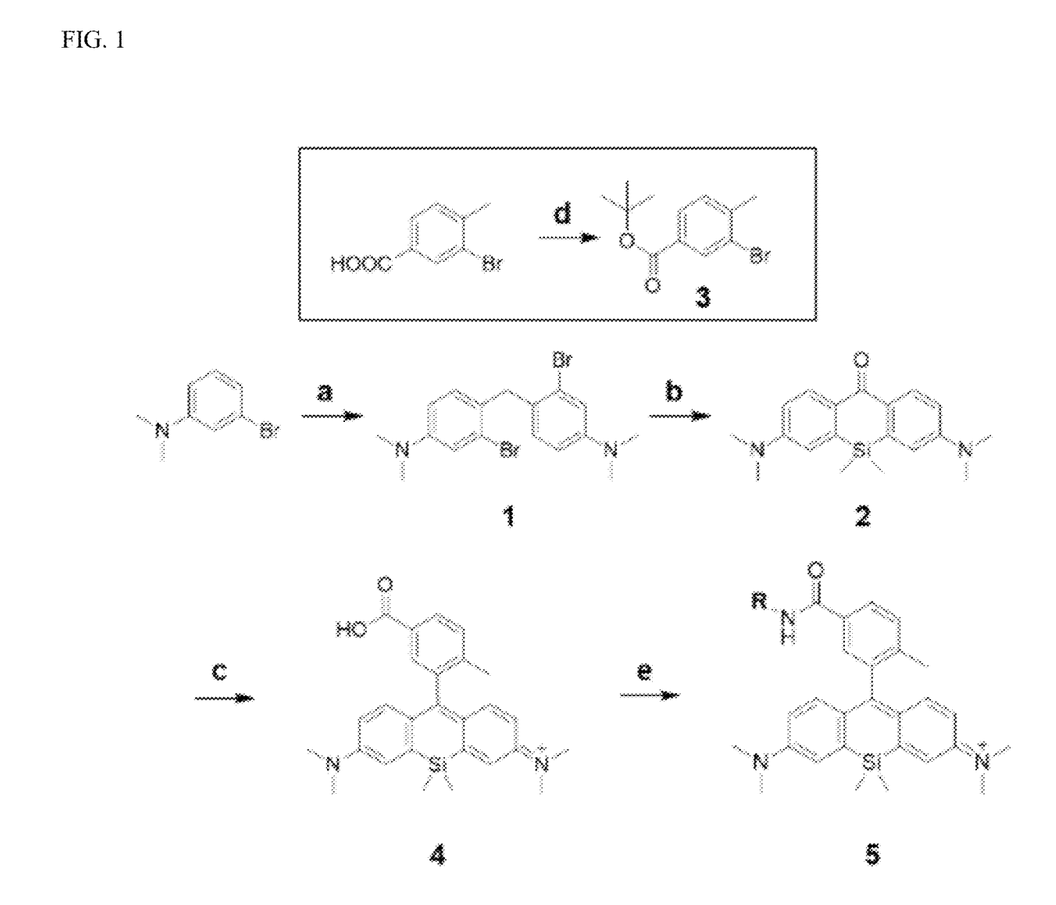
FIG. 1 is a schematic view showing a synthetic scheme for near-infrared (NIR) fluorescent mitochondria probes based on a silicon rhodamine core. a) Formaldehyde, AcOH, 60° C. 1.5 h, b) sec-BuLi, $SiCl_2Me_2$, THF, −78° C., then $KMnO_4$, acetone, 0° C., c) 3, tert-BuLi, THF, −78° C., then 6N HCl, 40° C., d) Di-tert-butyl dicarbonate, DMAP, THF, reflux, e) PyBOP, DIPEA, amine analogs, DMF, room temperature.

To determine the effect of probe hydrophobicity on the efficiency of targeting to mitochondria, the Pearson coefficient for colocalization of SiR-Mito probes and MitoTracker green, a commercial fluorescent mitochondrial bioprobe, was measured (FIG. 1). For the colocalization test, human cervical cancer HeLa cells were seeded on 96-well plates and incubated for 1 h with 1 μM of each different SiR-Mito probe and 0.5 μM MitoTracker green, washed briefly with 1×PBS, and imaged with a LEICA DMi8 fluorescent microscope using the 40× objective.

Figure 2:
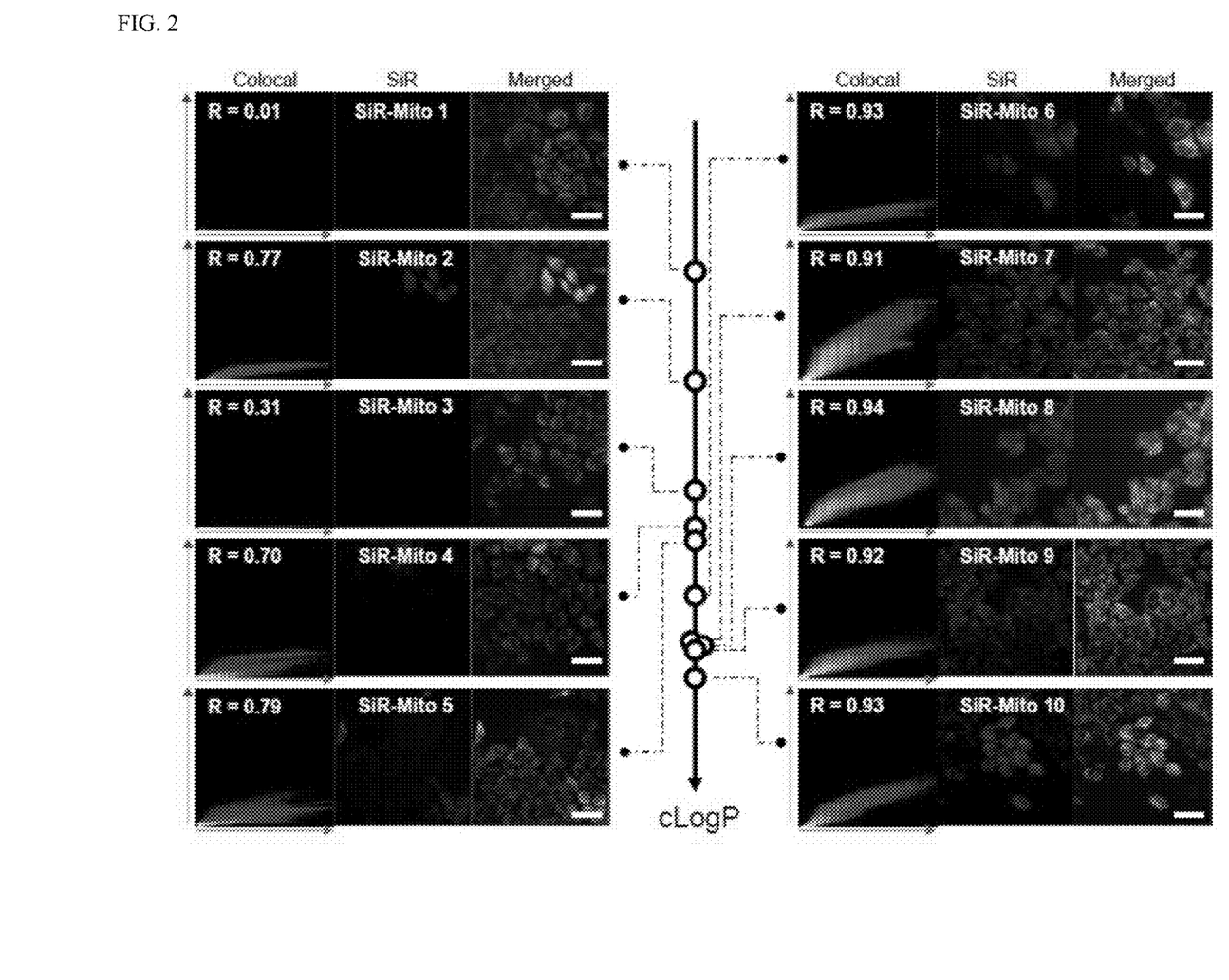
FIG. 2 shows a colocalization test in HeLa cells stained with SiR-Mito probes and MitoTracker Red. HeLa cells were incubated with cell culture media containing 1 μM SiR-Mito probe, and 0.5 μM MitoTracker green. After 1 h, HeLa cells were washed three times with 1×PBS for and observed with a LEICA DMi8 fluorescent microscope. Each experiment was observed using 512-542 nm emitter for FITC channel (for MitoTracker Green), and 663-738 nm exciter, 545-625 nm emitter for Cy5 channel (for SiR-Mito probes). Scale bar: 50 μm.
Figure 3:
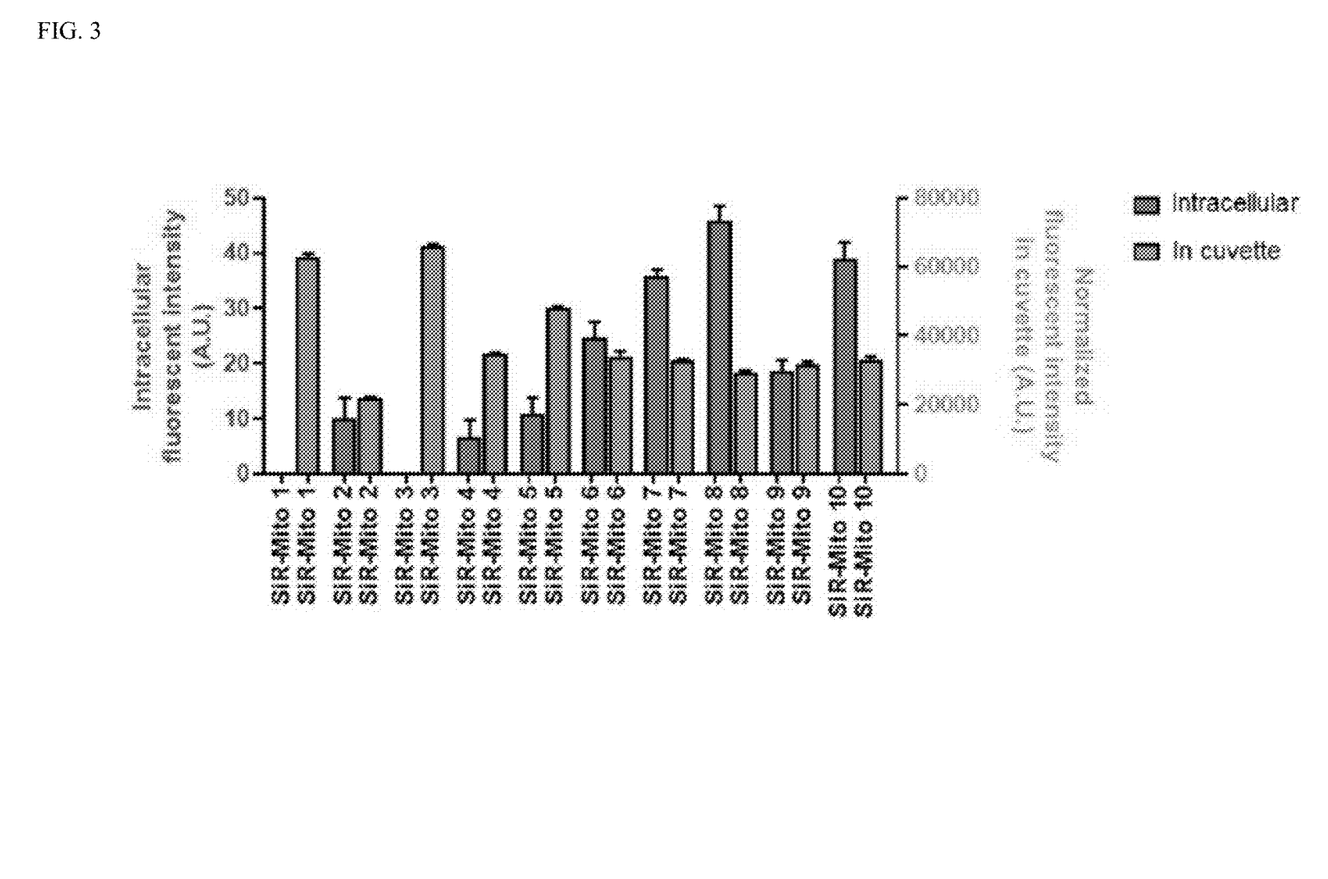
FIG. 3 shows a comparison between the fluorescent intensity of HeLa cells incubated with equal concentrations of individual probes (Left) and normalized fluorescent intensity (Right).

As a result, as shown in FIG. 2, the alteration of SiR-Mito probe hydrophobicity simply based on conjugation to different amines dramatically affected mitochondria localization. Pearson coefficient values were significantly different from probe to probe, ranging from 0.01 to 0.94. For example, the incubation of HeLa cells with SiR-Mito 1, exhibiting a cLogP value below 3, resulted in the absence of fluorescence signal in the SiR channel. The present inventors concluded that fluorescent conjugates containing SiR with cLogP values lower than 3 were too polar to enter the cells. Notably, SiR-Mito probes with cLogP values between 3.38 and 4.95 (from SiR-Mito 2 to SiR-Mito 5) were associated with moderate Pearson coefficients (0.31-0.79), whereas probes with cLogP values comprised between 5.50 and 6.33 (from SiR-Mito 6 to SiR-Mito 10) resulted in higher Pearson coefficient values (>0.9; Table 1). Therefore, the latter cLogP range appeared to be the most suitable for developing effective mitochondrial probes based on SiR fluorochromes. Notably, although the probes from SiR-Mito 6 to SiR-Mito 10 displayed similar Pearson coefficients (from 0.91 to 0.93), they exhibited different mean of intracellular fluorescence (FIG. 3).

The fluorescence intensities produced by equal concentrations (10-5 M in PBS) of the probes SiR-Mito 4 to SiR-Mito 10 were remarkably similar (FIG. 3), demonstrating a significant impact of probe hydrophobicity on mitochondrial accumulation. Among the probes, SiR-Mito 8 exhibited the highest Pearson coefficient as well as strongest intracellular fluorescence.

Example 4. Examination of Mitochondrial Specificity of SiR-Mito 8 in Live Cells

Mitochondrial specificity in live cells labeled with SiR-Mito 8 and MitoTracker green was examined by high-resolution imaging.

To this end, HeLa, and Hep3B cells were cultured in Dulbecco's modified eagle media (DMEM, GIBCO) containing 10% fetal bovine serum (FBS, GIBCO) and 1% penicillin (GIBCO) at 37° C. in a humidified incubator with 5% $CO_2$. For the fluorescence microscope imaging, cells were harvested using TrypLE™ Express (GIBCO) and resuspended in fresh culture medium. Harvested cells were seeded on a confocal dish with a density of $4.0×10^4$ cells/well. After 24 h incubation, cells were incubated with SiR-Mito 8 (1 μM) and Mitotracker green (0.5 uM) for 60 min. Cells were washed three times with 1×PBS and observed with inverted fluorescence microscope (DMi8, LEICA).

Figure 4:
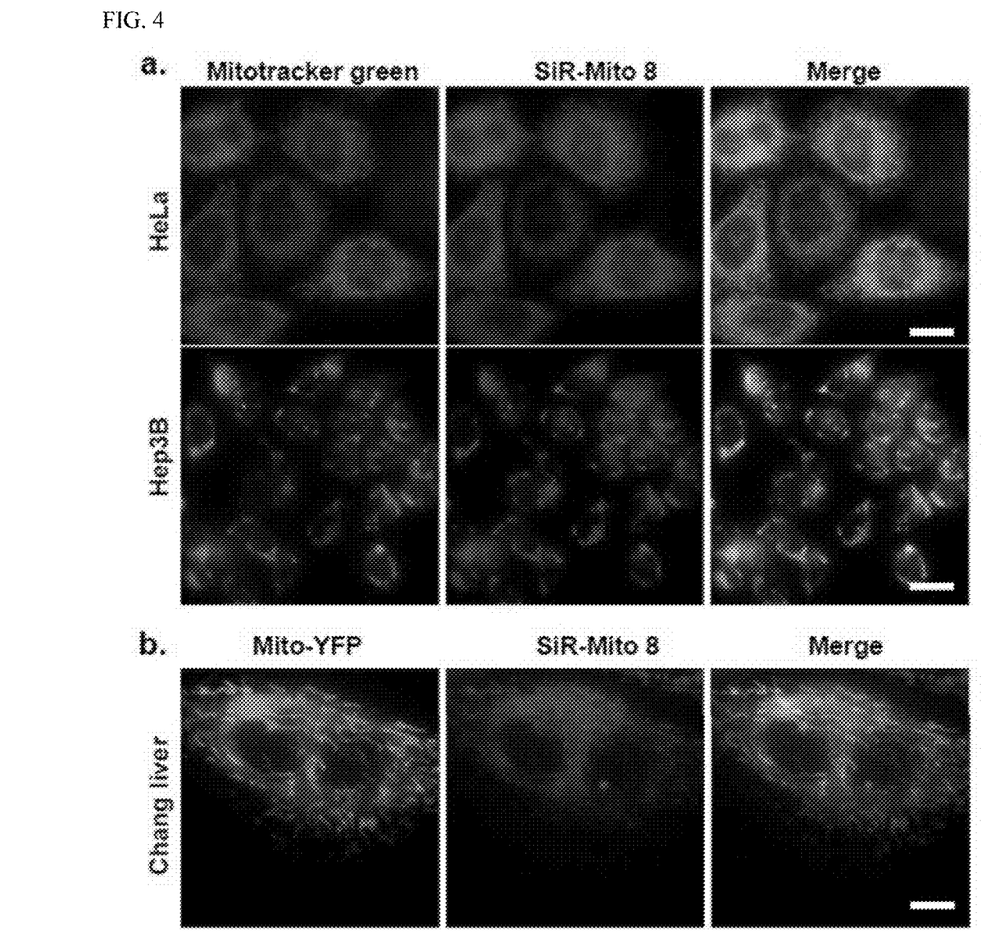
FIG. 4 shows high-resolution fluorescence imaging of mitochondria SiR-Mito 8. (a) HeLa and Hep3B cells were incubated with MitoTracker Green (0.5 μM), and SiR-Mito 8 (1 μM) for 1 h. After washing 3 times with fresh media, fluorescent live cell images were acquired with LEICA DMi8 microscope. (MitoTracker green: FITC channel, SiR-Mito 8: Cy 5 channel, Scale bar: 15 μm); (b) Chang liver cells expressing mitochondrial YFP were incubated with SiR-Mito 8 (1 μM) for 1 h. After washing 3 times with fresh media, fluorescent live cell images were acquired with LEICA DMi8 microscope. (Mitochondrial-YFP: Rhodamine channel, Scale bar: 15 μm).

As a result, it could be observed that both probes were highly co-expressed in the live cells (FIG. 4a), demonstrating mitochondrial specificity of SiR-Mito 8 in the live cells. Thus, SiR-Mito 8 may be used as a contrast agent.

Example 5. Mitochondrial Targeting Efficiency of SiR-Mito 8 in Live Cells

The mitochondrial targeting efficiency of SiR-Mito 8 in live cells was examined by high-resolution imaging.

To this end, Overexpression plasmid for Mitochondria-YFP was obtained from Catholic University (Seoul, Korea) and transfected into Chang liver cells. Stable clones expressing Mitochondria-YFP was selected using 0.25 mg/ml G418. Next, Mitochondria-YFP infected Chang liver cells were cultured in Dulbecco's modified eagle media (DMEM, GIBCO) containing 10% fetal bovine serum (FBS, GIBCO) and 1% penicillin (GIBCO) at 37° C. in a humidified incubator with 5% $CO_2$. For the fluorescence microscope imaging, cells were harvested using TrypLE™ Express (GIBCO) and resuspended in fresh culture medium. Harvested cells were seeded on a confocal dish with a density of $4.0 \times 10^4$ cells/well. After 24 h incubation, cells were incubated with SiR-Mito 8 (1 μM) for 60 min. Cells were washed three times with 1×PBS and observed with inverted fluorescence microscope (DMi8, LEICA).

As a result, as shown in FIG. 4b, it could be confirmed that SiR-Mito 8 exhibited high mitochondrial targeting efficiency.

Example 6. Verification of Mitochondrial Specificity of SiR-Mito 8 in Tumor Cell Line To verify the mitochondrial specificity of the SiR-Mito 8 probe, Hep3B human cancer cells were co-stained with a nuclear and a lysosomal tracer, in addition to SiR-Mito 8.

To this end, $6.0 \times 10^4$ human HCC cell line Hep3B cells were seeded on confocal dish and incubated for 2 days. After 2 days, Hep3B cells were incubated with Hoechst, 1 μM Lysotracker Red, and 1 μM SiR-Mito 8 contained media for 1 h. After the incubation, Hep3B cells were washed with cell culture media for three times and observed with inverted fluorescence microscope (DMi8, LEICA).

Figure 5:
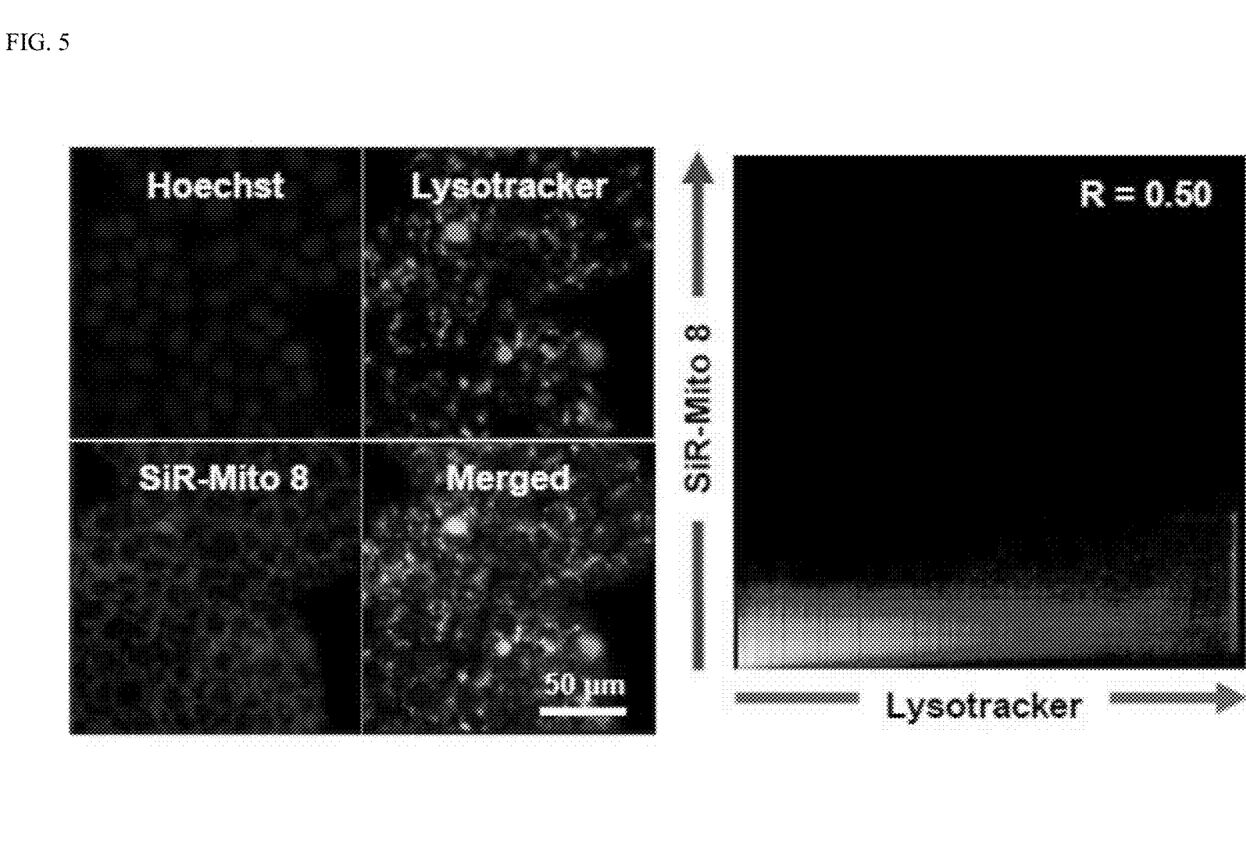
FIG. 5 shows the results of co-staining with SiR-Mito 8 and Lysotracker. Liver cancer Hep3B cells were incubated with Hoechst (0.01 μg/ml), Lysotracker red (1 μM), and SiR-Mito 8 (1 μM) for 1 h. After washing 3 times with fresh media, fluorescence live cell images were acquired with a LEICA DMi8 microscope (Left). The Pearson coefficient indicates that SiR-Mito 8 did not localize to other organelle such as lysosome (Right). Scale bar: 50 μm.
Figure 6:
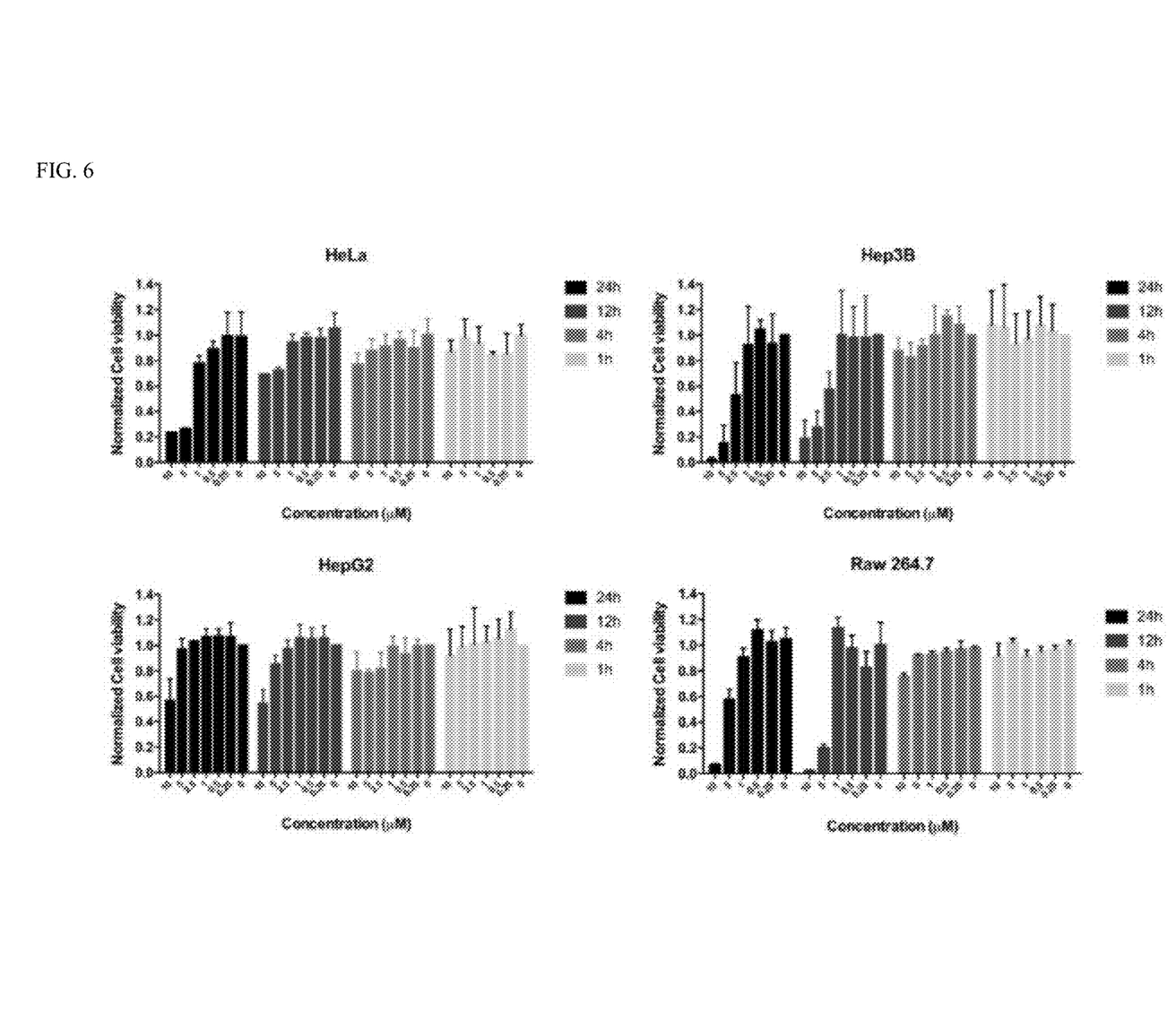
FIG. 6 shows the results of cytotoxicity test. HeLa, Hep3B, HepG2 and Raw 264.7 cells were incubated with SiR-Mito 8, concentration range from 0.25 μM to 10 μM, for 1, 4, 12, and 24 h. Viability of the cells was normalized by DMSO control.

The results of live cell imaging using Lysotracker Red indicated that SiR-Mito 8 exhibited high mitochondrial specificity, unlike other hydrophobic compounds known to accumulate in the lysosomes of tumor cells (FIG. 5).

Example 7. Cytotoxicity Test

In order to use SiR-Mito 8 as a potential NIR fluorescent tracer for mitochondrial staining, cytotoxicity of the probes was evaluated. HeLa, Hep3B, HepG2 and Raw 264.7 cells were incubated with SiR-Mito 8 at various concentrations (from 0.25 to 10.0 μM) and cytotoxicity was measured by a mitochondrial respiration viability assay.

Specifically, HeLa human cervical cancer cells, Hep3B and HepG2 human hepatocellular carcinoma cells, and Raw264.7 mouse macrophage cells were seeded into 96-well cell culture plates per well and allowed to adhere to the plates overnight. The cells were incubated with cell culture media containing each concentration of SiR-Mito 8 (0.25 μM to 10 μM) for 1, 4, 12 or 24 h. After incubation, CellTiter 96® Aqueous One Solution Cell Proliferation Assay (Promega) was added into each well. After 2 h, 490 nm absorption was measured with Cytation 3 microplate reader (BioTek). Cytotoxicity of SiR-Mito 8 was tested in triplicate in a single experiment, with each experiment being repeated at least three times.

As a result, it was confirmed that SiR-Mito 8 showed no acute cytotoxicity by SiR-Mito 8 up to the 24 hr time point with a moderate dose (less than 1 μM).

Example 8. Test for Comparison of Fluorescence Intensity Between Normal Cells and Cancer Cells It is well known that the membrane potential of mitochondria is significantly higher in cancer cells than in normal cells. Therefore, the present inventors envisioned that SiR-Mito 8 could differentiate cancer cells from normal cells without involving ligand conjugation. For fluorescent tumor imaging, human liver cancer Hep3B cells and the human hepatocyte line L02 were incubated with 1.0 μM SiR-Mito 8 for 1 hour, washed three times with cell growth media, and imaged using a LEICA DMi8 fluorescence microscope.

Specifically, Hep3B human liver cancer cells were cultured in Dulbecco's modified eagle media (DMEM, GIBCO) containing 10% fetal bovine serum (FBS, GIBCO) and 1% penicillin (GIBCO), and L02 or Chang human liver normal cells were cultured in Roswell Park Memorial Institute (RPMI, CAPRICORN) 1640 with L-Glutamine containing 10% FBS (GIBCO) and 1% Penicillin (HyClone) at 37° C. in a humidified incubator with 5% $CO_2$. For the fluorescence microscope imaging, cells were harvested using TrypLE™ Express (GIBCO) and resuspended in fresh culture medium. Harvested cells were seeded on a 96 black well plate (CORNING) with a density of $3.0 \times 10^4$ cells/well for cancer cells, and with a density of $4.0 \times 10^4$ cells/well for normal cells. After 24-hr incubation, for staining of mitochondria, cells were incubated with SiR-Mito 8 (1 μM) for 60 min. Cells were washed with cell culture media for three times and observed with inverted fluorescence microscope (DMi8, LEICA).

Figure 7:
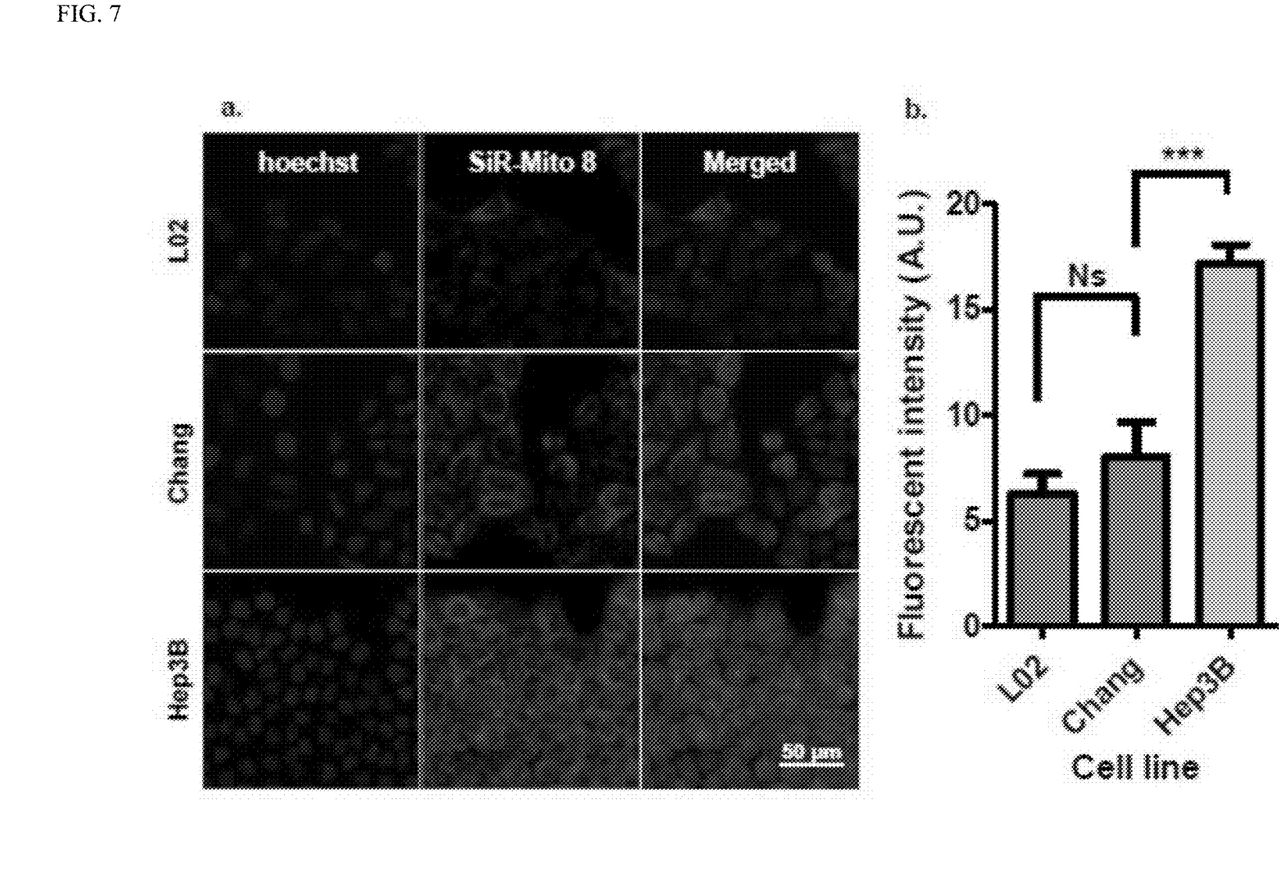
FIG. 7 shows cellular fluorescence images of Hep3B (liver cancer cells), L02 or Chang Liver cells (normal liver). (a) Cells were incubated with full growth media containing SiR-Mito 8 (1 μM) and Hoechst dye (0.01 μg/ml) for 1 h. The cells were washed 3 times with growth media and observed with a LEICA DMi8 fluorescent microscope. Cancer cells exhibit higher fluorescence intensity than normal cells. (b) Quantification of the fluorescence intensity of SiR-Mito 8 in L02, Chang liver and in Hep3B cells. Scale bar: 50 μm.

As a result, it was shown that the fluorescence intensity in the cancer cells was significantly higher than that in the normal cells (FIG. 7), indicating that the probe may be used for diagnosis of cancer cells or as a cancer cell-specific drug delivery carrier.

The present invention is directed to NIR bioprobes selectively staining mitochondria by systematic perturbation of hydrophobicity of the silicon rhodamine fluorophore. Ten different fluorescent SiR fluorochrome-based conjugates were synthesized and showed that probe hydrophobicity had a significant effect on the efficiency of mitochondria-specific staining. The optimal range of cLogP values for mitochondrial targeting by SiR fluorochromes was from 5.50 to 6.33. Among the 10 probes, SiR-Mito 8 exhibited the highest intracellular fluorescence intensity, as well as the strongest degree of colocalization with commercial fluorescent mitochondrial bioprobes in live cells. Moreover, SiR-Mito 8 was successfully applied to in vitro cancer-specific NIR imaging.

As is apparent from the above description, the fluorescent probe of the present invention has improved mitochondrial targeting efficiency compared to conventional probes due to a hydrophobic group attached to a silicon-rhodamine core, can detect mitochondria in living tissue with high sensitivity and specificity in a near-infrared (NIR) region (700 to 1,700 nm), and can acquire three-dimensional high-resolution biological images without harming the human body. Due to these advantages, the fluorescent probe can be used not only for mitochondrial detection in cells in the laboratory, but also as a contrast agent or a drug delivery carrier in cancer diagnosis and surgery.

Although the present invention has been described with reference to the above embodiments, it is to be understood that the scope of the present invention is not necessarily limited to these embodiments and various modifications are possible without departing from the scope and spirit of the present invention. Accordingly, the scope of the present invention should be construed to include all embodiments falling within the scope of the appended claims of the present invention.

What is claimed is:

1. A compound represented by the following Formula 1:

[Formula 1]

wherein R is 2-hydroxyl ethyl, ethyl, n-butyl, benzyl, phenyl ethyl, cyclohexylmethyl, tert-octyl, cyclooctyl, cyclohexylethyl, or 2-methylheptyl.

2. A probe for mitochondria targeting represented by Formula 1:

[Formula 1]

wherein R is 2-hydroxyl ethyl, ethyl, n-butyl, benzyl, phenyl ethyl, cyclohexylmethyl, tert-octyl, cyclooctyl, cyclohexylethyl, or 2-methylheptyl.

3. The probe of claim 2, wherein the probe is a near-infrared fluorescent probe.

4. The probe of claim 2, wherein the probe has a cLogP of 5.50 to 6.33.

5. A composition for mitochondrial detection comprising the probe of claim 2.

6. A contrast agent comprising the probe of claim 2.

7. A composition for cancer diagnosis comprising the probe of claim 2.

8. A drug delivery carrier comprising the probe of claim 2.

9. A method for visualizing mitochondria in cells in vitro, the method comprising steps of:
injecting the probe of claim 2 into cells in vitro; and
measuring a detectable fluorescent signal generated in the cells.

* * * * *